(12) United States Patent
Hirano

(10) Patent No.: US 7,419,656 B2
(45) Date of Patent: Sep. 2, 2008

(54) HAIR DYE COMPOSITIONS

(75) Inventor: Yuji Hirano, Tokyo (JP)

(73) Assignee: Kao Corporation, Tokyo (JP)

( * ) Notice: Subject to any disclaimer, the term of this patent is extended or adjusted under 35 U.S.C. 154(b) by 704 days.

(21) Appl. No.: 10/417,114

(22) Filed: Apr. 17, 2003

(65) Prior Publication Data

US 2003/0208858 A1  Nov. 13, 2003

(30) Foreign Application Priority Data

May 10, 2002  (JP) .............. 2002-135414

(51) Int. Cl.
*A61Q 5/10* (2006.01)
(52) U.S. Cl. .............. 424/70.6; 8/406; 8/408
(58) Field of Classification Search ........ None
See application file for complete search history.

(56) References Cited

U.S. PATENT DOCUMENTS

| | | | |
|---|---|---|---|
| 3,773,056 A | | 11/1973 | Kalopissis et al. |
| 5,617,883 A | * | 4/1997 | Savaides et al. ........ 132/205 |
| 5,665,778 A | * | 9/1997 | Semeria et al. ........ 514/613 |
| 5,976,516 A | | 11/1999 | Sakai et al. |
| 6,685,953 B1 | * | 2/2004 | Hoshino et al. ........ 424/401 |
| 6,733,541 B2 | * | 5/2004 | Pratt ........ 8/405 |

FOREIGN PATENT DOCUMENTS

| | | | |
|---|---|---|---|
| DE | 19907381 | * | 8/2000 |
| EP | 1 166 766 A1 | | 1/2002 |
| JP | 10-152419 | | 6/1998 |
| JP | 11-92349 | | 4/1999 |
| JP | 2002114666 | | 4/2002 |
| WO | WO 00/61097 | | 10/2000 |

OTHER PUBLICATIONS

U.S. Appl. No. 10/417,114, filed Apr. 17, 2003, Hirano.
U.S. Appl. No. 10/743,836, filed Dec. 24, 2003, Sakai, et al.
U.S. Appl. No. 10/743,833, filed Dec. 24, 2003, Sakai, et a.
U.S. Appl. No. 10/743,834, filed Dec. 24, 2003, Sakai, et al.
U.S. Appl. No. 10/731,249, filed Dec. 10, 2003, Hoshino, et al.
U.S. Appl. No. 10/694,775, filed Oct. 29, 2003, Hirano.
U.S. Appl. No. 10/694,774, filed Oct. 29, 2003, Hirano.
U.S. Appl. No. 09/926,270, filed Oct. 4, 2001, Hoshino, et al.
U.S. Appl. No. 10/418,112, filed Apr. 18, 2003, Hirano.
U.S. Appl. No. 10/417,993, filed Apr. 18, 2003, Hirano.
U.S. Appl. No. 11/563,935, filed Nov. 28, 2006, Hirano.

* cited by examiner

*Primary Examiner*—Jyothsna A Venkat
(74) *Attorney, Agent, or Firm*—Oblon, Spivak, McClelland, Maier & Neustadt, P.C.

(57) ABSTRACT

Provided are a hair dye composition comprising a diamide compound (1) and a dye; and a hair bleach composition comprising the diamide compound (1) and an oxidizing agent.

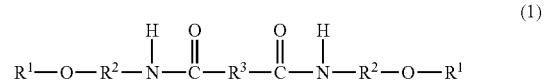

(1)

wherein, $R^1$: a $C_{1-12}$ hydrocarbon group which may be substituted by a hydroxy and/or alkoxy group, $R^2$: a divalent $C_{1-5}$ hydrocarbon group, and $R^3$: a divalent $C_{1-22}$ hydrocarbon group.

The hair dye composition or hair bleach composition according to the present invention suppresses hair damage during dyeing or bleaching, does not impair the moisture intrinsic to the hair, and provides excellent feeling upon use.

15 Claims, No Drawings

HAIR DYE COMPOSITIONS

TECHNICAL FIELD

The present invention relates to hair dye compositions and hair bleach compositions which can suppress hair damage during dyeing or bleaching, do not remove the moisture from the hair, and provide excellent feeling upon use.

BACKGROUND ART

Dyes contained in hair dye compositions include acid dyes, basic dyes and oxidation dyes. In order to cause effective penetration of these dyes into the hair, the pH of the compositions should be adjusted to a highly acidic or alkaline condition. The hair treated with such compositions however loses moisture and becomes rough to the touch, and moreover, it is known that split or broken hair easily generates upon daily hair care such as shampooing or styling. Hair bleach compositions which decompose, by the action of an oxidizing agent contained therein, melanin in the hair under an acidic condition, thereby bleaching the hair, also cause a similar hair damage and deterioration in the touch.

Although many hair dye compositions and bleach compositions put on the market usually contain a silicone, an animal or vegetable extract, or a conditioning polymer for the purpose of lessening damage to the hair, they have not yet exhibited sufficient effects.

DISCLOSURE OF THE INVENTION

An object of the present invention is therefore to provide a hair dye composition or a hair bleach composition capable of suppressing hair damage during dyeing or bleaching, not stripping the hair of essential moisture, and having excellent feeling upon use.

The present inventors have found that a marked reduction in hair damage can be accomplished by incorporating, in a hair dye composition or hair bleach composition, a diamide compound represented by the following formula (1):

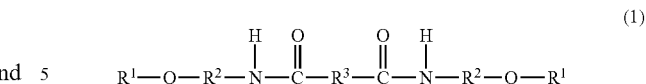

wherein, $R^1$ represents a linear or branched $C_{1-12}$ hydrocarbon group which may be substituted by a hydroxy and/or alkoxy group, $R^2$ represents a linear or branched divalent $C_{1-5}$ hydrocarbon group, and $R^3$ represents a linear or branched divalent $C_{1-22}$ hydrocarbon group.

In the present invention, there are thus provided a hair dye composition comprising (A) a diamide compound represented by the formula (1) and (B) a dye, and a hair bleach composition comprising (A) a diamide compound represented by the formula (1) and (C) an oxidizing agent.

BEST MODE FOR CARRYING OUT THE INVENTION

In the formula (1) representing the diamide compound serving as Component (A) in the present invention, preferred as $R^1$ are linear or branched $C_{1-12}$ alkyl groups which may be substituted by 1 to 3 substituents selected from a hydroxy group and $C_{1-6}$ alkoxy groups. Of these, more preferred are unsubstituted $C_{1-12}$ alkyl groups, and $C_{2-12}$ alkyl groups each substituted by one or two hydroxy groups, by one $C_{1-6}$ alkoxy group, or by one hydroxy group and one $C_{1-6}$ alkoxy group.

In the formula (1), preferred as $R^2$ are linear or branched $C_{2-5}$, particularly $C_{2-3}$ alkylene groups.

In the formula (1), preferred as $R^3$ are linear or branched divalent $C_{2-22}$ hydrocarbon groups, among which linear or branched $C_{11-22}$ alkylene groups and alkenylene groups having 1 to 4 double bonds are particularly preferred.

Particularly preferred diamide compounds as Component (A) include compounds having, as $R^1$, $R^2$ and $R^3$ in the formula (1), the above-exemplified preferred groups in combination. Specific examples of the particularly preferred diamide compounds (1) are shown below:

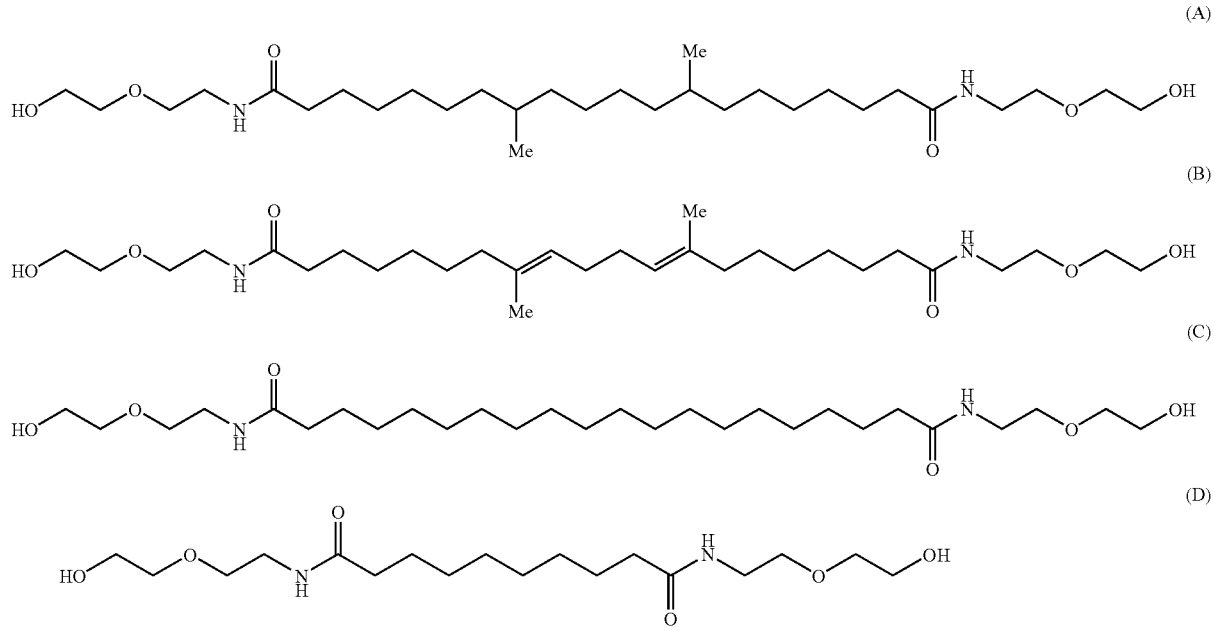

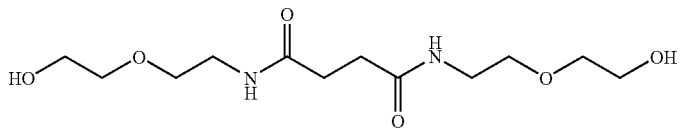

(E)

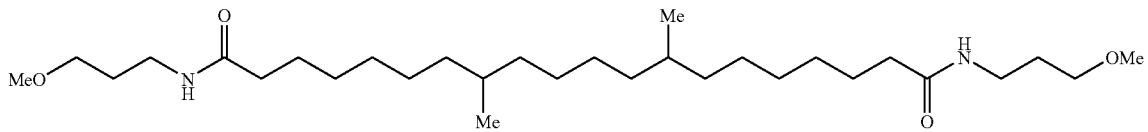

(F)

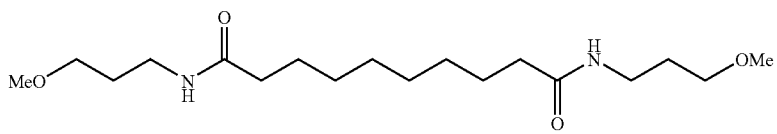

(G)

The diamide compounds (1) can be prepared by a known amide synthesizing process. For example, the intended diamide compound (1) can be prepared efficiently at a low cost by condensing the corresponding dicarboxylic acid (2) or reactive derivative thereof (ester, acid halide, acid anhydride, or the like) with an amine (3) in accordance with the following reaction scheme (International Publication No. 00/61097 brochure):

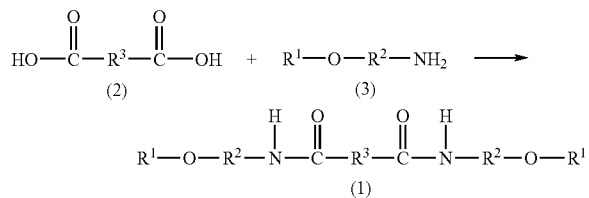

As Component (A), two or more diamide compounds (1) may be used in combination. From the viewpoints of sufficiently suppressing hair damage and at the same time, avoiding deterioration in feeling upon use, the content of the diamide compound (1) is preferably from 0.01 to 30 wt. %, more preferably from 0.1 to 20 wt. %, especially preferably from 0.5 to 15 wt. % based on the composition just prior to use.

Examples of the dye to be incorporated as Component (B) in the hair dye composition of the present invention include oxidative dye intermediates and direct dyes.

As the oxidative dye intermediates, known developers and couplers ordinarily employed for oxidation type hair dyes are usable. Examples of the developer include p-phenylenediamines having one or several groups selected from $NH_2$—, NHR— and $NR_2$— groups (wherein, R represents a $C_{1-4}$ alkyl or hydroxyalkyl group) such as p-phenylenediamine, p-toluylenediamine, N-methyl-p-phenylenediamine, N,N-dimethyl-p-phenylenediamine, N,N-diethyl-2-methyl-p-phenylenediamine, N-ethyl-N-(hydroxyethyl)-p-phenylenediamine, chloro-p-phenylenediamine, 2-(2'-hydroxyethylamino)-5-aminotoluene, N,N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives; p-aminophenols such as p-aminophenol, 2-methyl-4-aminophenol, 3-methyl-4-aminophenol, 2-chloro-4-aminophenyl, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,4-diaminophenol and 5-aminosalicylic acid; and o-aminophenols and o-phenylenediamines.

Examples of the coupler include α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, 5-(2'-hydroxyethylamino)-4-methoxy-2-methylphenol, hydroquinone, 2,4-diaminoanisole, m-toluylenediamine, 4-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxy-3-quinolone, m-aminophenol, 4-chlororesorcin, 2-methylresorcin, 2,4-diaminophenoxyethanol, 2,6-diaminopyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine and 4,6-diamino-2-hydroxypyrimidine.

As each of the developer and coupler, two or more of the above-exemplified substances may be used in combination. Each of the developer and coupler is added preferably in an amount of from 0.01 to 5 wt. %, especially preferably from 0.1 to 4 wt. % based on the whole composition having a first part and a second part mixed therein.

As the direct dye, known acid dyes, basic dyes, disperse dyes and reactive dyes usable for a hair dye can be employed. Examples of the acid dye include Acid Red 27 (C.I. 16185), Acid Red 51 (C.I. 45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87 (C.I. 45380), Acid Red 92 (C.I. 45410), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Solvent Green 7 (C.I. 59040), Acid Green 5 (C.I. 42095), Acid Blue 5 (C.I. 42052), Acid Blue 9 (C.I. 42090), Acid Orange 24 (C.I.

20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685) and Brilliant Black 1 (C.I. 28440).

Examples of the basic dye include Basic Blue 7 (C.I. 42595), Basic blue 16 (C.I. 12210), Basic Blue 22 (C.I. 61512), Basic Blue 26 (C.I. 44045), Basic Blue 99 (C.I. 56059), Basic Blue 117, Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 51, Basic Red 76 (C.I. 12245), Basic Red 118 (C.I. 12251:1), Basic Orange 31, Basic Yellow 28 (C.I. 48054), Basic Yellow 57 (C.I. 12719), Basic Yellow 87 and Basic Black 2 (C.I. 11825), basic dyes, as described in Japanese Patent Publication No. Sho 58-2204 and Japanese Patent Application Laid-Open No. Hei 9-118832, which contain, at the side chain of the aromatic ring thereof, a quaternized nitrogen atom, and basic dyes, as described in Japanese-Language Laid-Open Publication (PCT) No. Hei 10-502946 and Japanese Patent Applications Laid-Open Nos. Hei 10-182379 and Hei 11-349457.

Examples of the direct dyes other than acid dyes and basic dyes include 2-amino-3-nitrophenol, 2-amino-4-nitrophenol, 2-amino-5-nitrophenol, 4-amino-3-nitrophenol, 2-amino-6-chloro-4-nitrophenol, 4-hydroxypropylamino-3-nitrophenol, 3-nitroparahydroxyethylaminophenol, 2-nitroparaphenylenediamine, 4-nitroorthophenylenediamine, 4-nitrometaphenylenediamine, 6-nitroorthotoluidine, 6-nitroparatoluidine, hydroxyethyl-2-nitroparatoluidine, N,N'-bis(2-hydroxyethyl)-2-nitroparaphenylenediamine, 2-chloro-5-nitro-N-hydroxyethylparaphenylenediamine, 2-nitro-5-glycerylmethylaniline, 3-methylamino-4-nitrophenoxyethanol, N-ethyl-3-nitroPABA, picramic acid, 2-hydroxyethylpicramic acid, 4-nitrophenylaminoethylurea, Solvent Violet 13(C.I.60725), Solvent Yellow 44 (C.I.56200), Disperse Red 17 (C.I.11210), Disperse Violet 1 (C.I.61100), Disperse Violet 4 (C.I. 61105), Disperse Blue 3 (C.I. 61505), Disperse Blue 7 (C.I. 62500), HC Blue No. 2, HC Blue No. 8, HC Orange No. 1, HC Orange No. 2, HC Red No. 1, HC Red No. 3, HC Red No. 7, HC Red No. 8, HC Red No. 10, HC Red No. 11, HC Red No. 13, HC Red No. 16, HC Violet No. 2, HC Yellow No. 2, HC Yellow No. 5, HC Yellow No. 6, HC Yellow No. 7, HC Yellow No. 9, and HC Yellow No. 12.

As the direct dye, two or more of the above-exemplified ones may be used in combination, and the total amount thereof preferably falls within a range of from 0.001-5 wt. %, particularly preferably from 0.01-4 wt. %, each based on the whole composition having the first and second agents mixed therein. The direct dye may be used in combination with the oxidative dye.

Examples of oxidizing agent serving as component (C) in the present invention include hydrogen peroxide, urea peroxide, bromates of an alkali metal and peracid salts of an alkali metal (perbromates, persulfates, perborates, etc.), with hydrogen peroxide being especially preferred. From the viewpoints of sufficient hair bleaching or dyeing effects and a reduction in stimulus to the scalp, the amount of the oxidizing agent preferably falls within a range of from 2 to 12 wt. %, in terms of hydrogen peroxide, based on the whole composition having the first part and second part mixed therein. The oxidizing agent may be incorporated not only in the hair bleach composition but also in the hair dye composition, particularly in the second part of a two-part system hair dye composition.

To the hair dye composition or bleach composition of the present invention, components ordinarily employed in the field of cosmetics can be added further depending on the using purpose. Examples of such optional components include natural or synthetic high-molecular compounds, fatty acids, oils and fats, hydrocarbons, higher alcohols, monohydric or polyhydric alcohols, silicone derivatives, nonionic surfactants, amine oxides, amino acid derivatives, protein derivatives, antiseptics, metal sequestering agents, antioxidants, stabilizers for hydrogen peroxide, vegetable extracts, vitamins, colorants, pigments, ultraviolet absorbers and pH regulators.

The hair dye composition or hair bleach composition according to the present invention may be provided as one-part system compositions using a direct dye, for example, color shampoos, color rinses and hair manicures, or two- or three-part system compositions such as oxidizing type hair dye or hair bleach. Sometimes, they may be mixed at a predetermined ratio upon use.

EXAMPLES

Examples 1 to 5, and Comparative Examples 1 and 2

Hair dye compositions as listed in Tables 1 to 3 were prepared and "moisture loss" and "ratio of generated split hair" after the hair was treated with each composition were evaluated to study the effect of the invention.

Evaluation Method and Criteria (1) Prevention of Moisture Loss

A bundle (10 g) made of the hair of a Japanese female was dyed with each composition in a predetermined manner, followed by organoleptic evaluation by a panel of 10 experts to examine the moisture loss. Average evaluation scores in accordance with the below-described criteria were judged as A, B and C when the average scores were 2.4 or greater, 1.6 to 2.3 and 1.0 to 1.5, respectively.

<Evaluation Criteria>
There is no feel of moisture loss: 3
There is some feel of moisture loss: 2
There is a feel of moisture loss: 1

(2) Ratio of Generated Split Hair

A 16-cm long hair bundle (about 0.1 g) made of 100 hairs of a Japanese female was prepared. It was treated with each composition of the Examples and the Comparative Examples by a predetermined method. Then, a brushing stimulus was applied to the resulting hair bundle with a rotating hairbrush driven by a motor at a rotation speed of 100 times/minute for 60 minutes. The number (D) of split or cut hairs was then counted. The split hair-generation ratio was determined from the following formula:

Split hair-generation ratio (%)=$D \div 100 \times 100 = D$

Hair Manicure (Examples 1 and 2, and Comparative Example 1)

A hair dye composition (hair manicure) was prepared by adding, in portions, a solution of Component (1) dissolved in the whole amount of Component (5) to a mixture composed of Component (2) and Components (6) to (8), wherein each component is shown in Table 1; stirring the resulting mixture; adding to the mixture while stirring another mixture which had been obtained by adding Component (4) to Component (3); and then stirring the resulting mixture for about one hour at room temperature.

To a tress for evaluation, the resulting composition was applied at a hair:composition bath ratio (weight ratio) of 1:1 to wet the tress with the composition. After the tress was allowed to stand at room temperature for 25 minutes, it was rinsed to remove the composition, shampooed once with a commercially available shampoo and then dried with a dryer.

Evaluation results are shown in Table 1.

TABLE 1

|   |   | Example 1 | Example 2 | Comparative Example 1 |
|---|---|---|---|---|
| (1) | Diamide compound (A) | 1.0 | 2.0 | — |
| (2) | Acid Orange 7 | 0.5 | 0.5 | 0.5 |
| (3) | Benzyl alcohol | 10.0 | 10.0 | 10.0 |
| (4) | Xanthan gum | 1.5 | 1.5 | 1.5 |
| (5) | Ethanol | 15.0 | 15.0 | 15.0 |
| (6) | Sodium hydroxide | q.s. (pH 2.9) | q.s. (pH 2.9) | q.s. (pH 2.9) |
| (7) | Lactic acid | 4.5 | 4.5 | 4.5 |
| (8) | Water | Balance | Balance | Balance |
|   | Total | 100 wt. % | 100 wt. % | 100 wt. % |
|   | Evaluation |   |   |   |
|   | Split hair-generation ratio | 20 | 12 | 27 |
|   | Prevention of moisture loss | A | A | B |

Two-Part System Permanent Hair Dye Compositions (Examples 3 to 5 and Comparative Example 2)

An aqueous phase was prepared by mixing Component (14) with Components (2) to (4) and (10) to (12) and a portion (5 wt. %) of Component (13), wherein each component is shown in Table 2, and dissolving the components by heating to 70° C. and maintaining thereat. To the remaining portion (2 wt. %) of Component (13) were added Components (1) and (5) to (9) and the resulting oil phase was uniformly dissolved by heating to 70° C. The oil phase was gradually added to the aqueous phase. After stirring at 70° C. for 20 minutes, the reaction mixture was cooled gradually to room temperature, whereby the first part of the two-part system permanent hair dye was prepared.

The second part of the two-part system permanent hair dye having the composition as shown in Table 3 was prepared separately.

A 1:1 (weight ratio) uniform mixture of each of predetermined combinations of the first part and the second part as shown in Table 4 was applied to a tress for evaluation at a hair: composition bath ratio (weight ratio) of 1:1 and the resulting tress was allowed to stand at room temperature for 25 minutes. The tress was rinsed with water to remove the hair dye, shampooed once with a commercially available shampoo, and dried with a hair dryer.

Evaluation results are shown in Table 4.

TABLE 2

|   |   | First part A | First part B |
|---|---|---|---|
| (1) | Diamide compound (B) | 2.0 | — |
| (2) | p-Phenylenediamine | 2.0 | 2.0 |
| (3) | o-Aminophenol | 1.0 | 1.0 |
| (4) | m-Phenylenediamine | 0.2 | 0.2 |
| (5) | Cetanol | 5.5 | 5.5 |
| (6) | Polyoxyethylene (40) cetyl ether | 2.5 | 2.5 |
| (7) | Polyoxyethylene (2) Cetyl ether | 3.0 | 3.0 |
| (8) | Liquid paraffin | 0.4 | 0.4 |
| (9) | Sodium sulfite | 0.3 | 0.3 |
| (10) | Monoethanolamine | 2.5 | 2.5 |
| (11) | Ammonium chloride | 0.5 | 0.5 |
| (12) | Ammonia (28 wt. %) | q.s. (pH 9) | q.s. (pH 9) |
| (13) | Propylene glycol | 7.0 | 7.0 |
| (14) | Purified water | Balance | Balance |
|   | Total | 100 wt. % | 100 wt.% |

TABLE 3

|   |   | Second part A | Second part B |
|---|---|---|---|
| (1) | Diamide compound (B) | 1.0 | — |
| (2) | Hydrogen peroxide (35 wt. %) | 15.0 | 15.0 |
| (3) | Cetanol | 5.0 | 5.0 |
| (4) | Polyoxyethylene (20) cetyl ether | 4.5 | 4.5 |
| (5) | Propylene glycol | 6.0 | 6.0 |
| (6) | Liquid paraffin | 0.2 | 0.2 |
| (7) | Phosphoric acid | q.s. (pH 3.5) | q.s. (pH 3.5) |
| (8) | Purified water | Balance | Balance |
|   | Total | 100 wt. % | 100 wt. % |

TABLE 4

|   | Example 3 | Example 4 | Example 5 | Comparative Example 2 |
|---|---|---|---|---|
| Combination |   |   |   |   |
| First part | A | B | A | B |
| Second part | B | A | A | B |
| Split hair-generation ratio (%) | 29 | 28 | 22 | 38 |
| Prevention of moisture loss | A | A | A | C |

Example 6

Two-Part System Permanent Hair Dye Composition (Cream)

The first part having the below-described composition and the second part A as shown in Table 3 were mixed in equal amounts and provided for use.

| First part | (wt. %) |
|---|---|
| Diamide compound (A) | 1.5 |
| p-Phenylenediamine | 2.0 |
| o-Aminophenol | 1.0 |
| m-Phenylenediamine | 0.5 |
| Cetanol | 5.5 |
| Polyoxyethylene (40) cetyl ether | 2.5 |
| Polyoxyethylene (2) cetyl ether | 3.0 |

-continued

| First part | (wt. %) |
| --- | --- |
| Liquid paraffin | 0.2 |
| Sodium sulfite | 0.3 |
| Monoethanolamine | 2.5 |
| Ammonia (28 wt. %) | Amount to adjust the pH to 9.0 |
| Propylene glycol | 5.0 |
| Benzyl alcohol | 3.0 |
| Amino-modified silicone emulsion ("SM8704C", product of Dow Corning Toray Silicone) | 0.5 |
| Keratin hydrolysate ("Promois WK-H" product of Seiwa Kasei) | 0.5 |
| Olive oil | 0.2 |
| Perfume | q.s. |
| Purified water | Balance |
| Total | 100.0 |

Example 7

Two-Part System Permanent Hair Dye Composition (Liquid)

The first part and second part having the compositions as described below were mixed in equal amounts and provided for use.

| First part | (wt. %) |
| --- | --- |
| Diamide compound (C) | 1.0 |
| p-Phenylenediamine | 2.0 |
| o-Aminophenol | 1.0 |
| m-Phenylenediamine | 0.5 |
| Oleic acid | 4.0 |
| Cetanol | 0.5 |
| Oleyl alcohol | 1.0 |
| Polyoxyethylene (20) dodecyl ether | 8.0 |
| Polyoxyethylene (9) dodecyl ether | 6.0 |
| Polyoxyethylene (3) dodecyl ether | 6.0 |
| Propylene glycol | 8.0 |
| Ethanol | 12.0 |
| 2-Benzyloxyethanol | 4.0 |
| Monoethanolamine | 2.5 |
| Aqueous ammonia (28 wt. %) | Amount to adjust the pH to 9.0 |
| Anhydrous sodium sulfite | 0.3 |
| Ethylenediaminetetraacetic acid tetrasodium salt dihydrate | 0.1 |
| Polyether-modified silicone ("KF-6005", product of Shin'etsu Chemical) | 0.5 |
| Jojoba oil | 0.1 |
| Perfume | q.s. |
| Purified water | Balance |
| Total | 100.0 |

| Second part | (wt. %) |
| --- | --- |
| Diamide compound (C) | 1.0 |
| Hydrogen peroxide (35 wt. %) | 15.0 |
| Cetanol | 1.5 |
| Polyoxyethylene (20) cetyl ether | 0.8 |
| Polyoxyethylene (2) cetyl ether | 0.2 |
| Glycerin | 0.5 |

-continued

| Second part | (wt. %) |
| --- | --- |
| Phosphoric acid | Amount to adjust the pH to 9.0 |
| Purified water | Balance |
| Total | 100.0 |

Example 8

Two-Part System Bleach Composition

The first part and second part having the compositions as shown below were mixed in equal amounts and provided for use.

| First part | (wt. %) |
| --- | --- |
| Diamide compound (A) | 2.5 |
| Aqueous ammonia (28 wt. %) | 5.0 |
| Ammonium bicarbonate | Amount to adjust the pH to 9.0 |
| Oleic acid | 1.5 |
| Oleyl alcohol | 1.0 |
| Polyoxyethylene (20) cetyl ether | 8.0 |
| Polyoxyethylene (9) cetyl ether | 5.0 |
| Polyoxyethylene (3) cetyl ether | 5.0 |
| Ethanol | 8.0 |
| Propylene glycol | 8.0 |
| Amino-modified silicone emulsion ("SM8704C", product of Dow Corning Toray Silicone) | 0.5 |
| Cationized keratin hydrolysate ("Promois WK-Q"; product of Seiwa Kasei) | 0.2 |
| Perfume | q.s. |
| Purified water | Balance |
| Total | 100.0 |

| Second part | (wt. %) |
| --- | --- |
| Hydrogen peroxide (35 wt. %) | 15.0 |
| Polyoxyethylene (20) cetyl ether | 1.0 |
| Polyether-modified silicone ("KF-6005", product of Shin'etsu Chemical) | 0.5 |
| Phosphoric acid | Amount to adjust the pH to 3.2 |
| Purified water | Balance |
| Total | 100.0 |

Example 9

Hair Manicure Composition (Aerosol Type)

A stock solution and a propellant each having the below-described composition were filled at a stock solution:propellant weight ratio of 85:15 in a predetermined aerosol container.

|  | (wt. %) |
| --- | --- |
| Stock solution | |
| Diamide compound (C) | 2.0 |
| Acid orange 7 | 0.8 |
| 2-Benzyloxyethanol | 5.0 |
| Ethanol | 10.0 |
| 1,3-Butylene glycol | 5.0 |
| Xanthan gum | 1.2 |
| Sodium hydroxide | Amount to adjust the pH to 3.0 |
| Lactic acid | 4.5 |
| Polyether-modified silicone ("KF-6005", product of Shin'etsu Chemical) | 0.5 |
| Perfume | q.s. |
| Purified water | Balance |
| Total | 100.0 |
| Propellant | |
| LPG (3.5 kg/cm$^2$) | 85.0 |
| Dimethyl ether | 15.0 |
| Total | 100.0 |

Any one of the compositions obtained in Examples 6 to 9 caused markedly little damage to the hair and, at the same time, did not impair moisture feeling of the hair.

The invention claimed is:

1. A hair dye composition comprising the following components (A), (B) and (C): (A) a diamide compound represented by the following formula

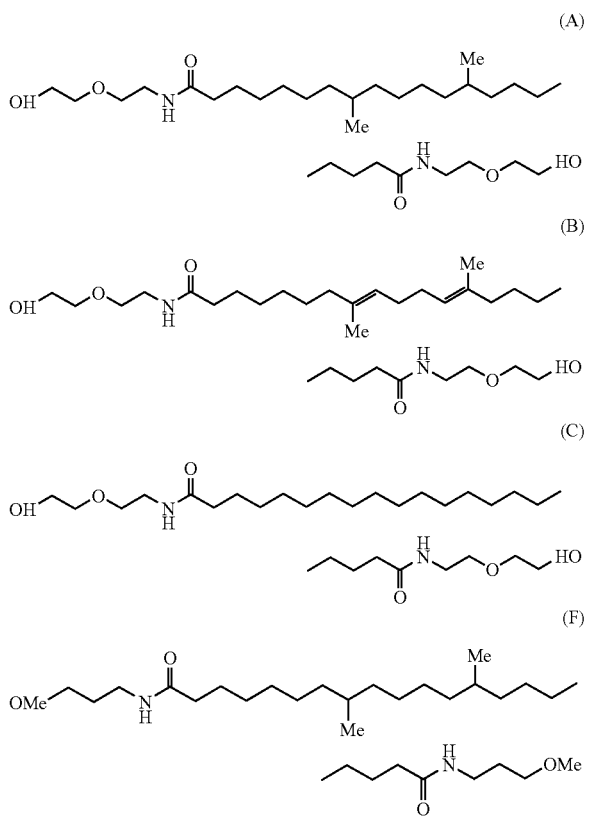

(B) a dye selected from at least one of the group consisting of an oxidative dye intermediate comprising 0.01 to 5 wt. % of a developer and 0.01 to 5 wt. % of a coupler; and 0.001-5 wt. % of a direct dye; and (C) an oxidizing agent wherein said hair dye composition is a two-part system and said oxidizing agent is incorporated in a second part of a two-part system hair dye composition.

2. The hair dye composition of claim 1, wherein said developer is present and is at least one selected from the group consisting of p-phenylenediamines having one or several groups selected from $NH_2$—, NHR— and $NR_2$— groups (wherein, R represents a $C_{1-4}$ alkyl or hydroxyalkyl group), 2,5-diaminopyridine derivatives, p-aminophenols, o-aminophenols and o-phenylenediamines.

3. The hair dye composition of claim 2, wherein said developer is at least one developer selected from the group consisting of p-phenylenediamine, p-toluylenediamine, N-methyl-p-phenylenediamine, N,N-dimethyl-p-phenylenediamine, N,N-diethyl-2-methyl-p-phenylenediamine, N-ethyl-N-(hydroxyethyl)-p-phenylenediamine, chloro-p-phenylenediamine, 2-(2'-hydroxyethylamino)-5-aminotoluene, N,N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p- phenylenediamine-, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives; p-aminophenol, 2-methyl-4-aminophenol, 3-methyl-4-aminophenol, 2-chloro-4-aminophenyl, 3-chloro-4-aminophenol, 2,6-dimethyl-4-amino-pheno-1,3,5-dimethyl-4-aminophenol, 2,3-dimethyl-4-aminophenol, 2,5-dimethyl-4-aminophenol, 2,4-diaminophenol and 5-aminosalicylic acid; o-aminophenols and o-phenylenediamines.

4. The hair dye composition of claim 1, wherein a coupler is present and is at least one selected from the group consisting α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, 5-(2'-hydroxyethylamino)-4-methoxy-2-methylphenol, hydroquinone, 2,4-diaminoanisole, m-toluylenediamine, 4-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxy-3-quinolone, m-aminophenol, 4-chlororesorcin, 2-methylresorcin, 2,4-diaminophenoxyethanol, 2,6-diaminopyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine and 4,6-diamino-2-hydroxypyrimidine.

5. The hair dye composition of claim 1, wherein said dye is a direct dye selected from the group consisting of an acid dye, a basic dye, a disperse dye, a reactive dye and a mixture thereof.

6. The hair dye composition of claim 5, wherein said dye is an acid dye selected from the group consisting of Acid Red 27 (C.I. 16185), Acid Red 51 (C.I. 45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87 (C.I.

45380), Acid Red 92 (C.I. 45410), Acid Orange 7 (C.I. 15510), Acid Red 95 (CA. 45425), Acid Yellow 73 (C.I. 45350), Acid Yellow 3 (C.I. 47005), Acid Green 25 (C.I. 61570), Solvent Green 7 (C.I. 59040), Acid Green 5 (C.I. 42095), Acid Blue 5 (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685), Brilliant Black 1 (C.I. 28440) and a mixture thereof.

7. The hair dye composition of claim 5, wherein said dye is an basic dye selected from the group consisting of Basic Blue 7 (C.I. 42595), Basic blue 16 (C.I. 12210), Basic Blue 22 (C.I. 61512), Basic Blue 26 (C.I. 44045), Basic Blue 99 (C.I. 56059), Basic Blue 117, Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 51, Basic Red 76 (C.I. 12245), Basic Red 118 (C.I. 12251:1), Basic Orange 31, Basic Yellow 28 (C.I. 48054), Basic Yellow 57 (C.I. 12719), Basic Yellow 87, Basic Black 2 (C.I. 11825) and a mixture thereof.

8. The hair dye composition of claim 5, wherein said dye is a direct dye other than an acid dye or a basic dye and is selected from the group consisting of 2-amino-3-nitrophenol, 2-amino-4-nitrophenol, 2-amino-5-nitrophenol, 4-amino-3-nitrophenol, 2-amino-6-chloro-4-nitrophenol, 4-hydroxypropylamino-3-nitrophenol, 3-nitroparahydroxyethylaminopheno-1, 2-nitroparaphenylenediamine, 4-nitroorthophenylenediamine, 4-nitrometaphenylenediamine, 6-nitroorthotoluidine, 6-nitroparatoluidine, hydroxyethyl-2-nitroparatoluidine, N,N'-bis(2-hydroxyethyl)-2-nitroparaphenylenediamine, 2-chloro-5-nitro-N-hydroxyethylparaphenylenediamine, 2-nitro-5-glycerylmethylaniline, 3-methylamino-4-nitrophenoxyethanol, N-ethyl-3-nitroPABA, picramic acid, 2-hydroxyethylpicramic acid, 4-nitrophenylaminoethylurea, Solvent Violet 13 (C.I.60725), Solvent Yellow 44 (C.I.56200), Disperse Red 17 (C.I.11210), Disperse Violet 1 (C.I.61100), Disperse Violet 4 (C.I.61105), Disperse Blue 3 (C.I.61505), Disperse Blue 7 (C.I.62500), HC Blue No. 2, HC Blue No. 8, HC Orange No. 1, HC Orange No. 2, HC Red No. 1, HG Red No. 3, HC Red No. 7, HC Red No. 8, HC Red No. 10, HC Red No. 11, HC Red No. 13, HG Red No. 16, HG Violet No. 2, HG Yellow No. 2, HG Yellow No. 5, HG Yellow No. 6, HG Yellow No. 7, HG Yellow No. 9, HG Yellow No. 12 and a mixture thereof.

9. The hair dye composition of claim 1, wherein said diamide compound is represented by the following formula:

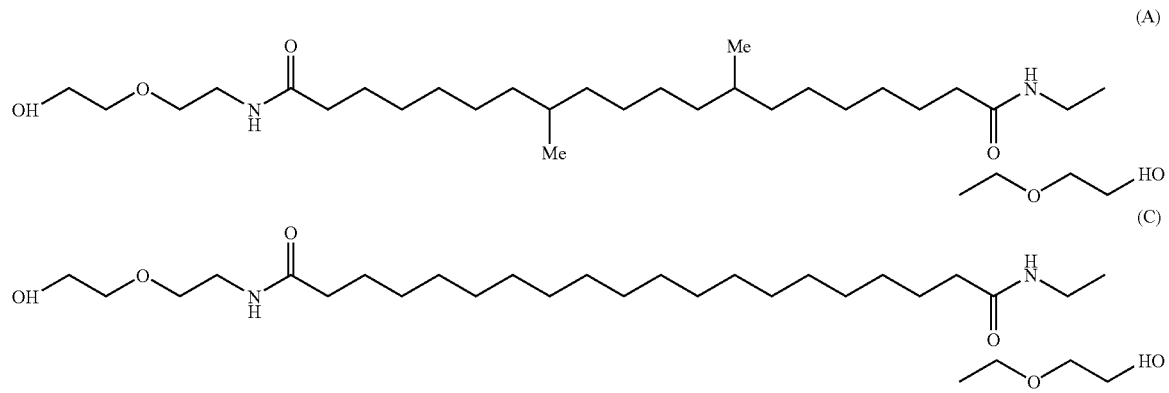

10. The hair dye composition of claim 1, wherein said diamide compound is represented by the following formula:

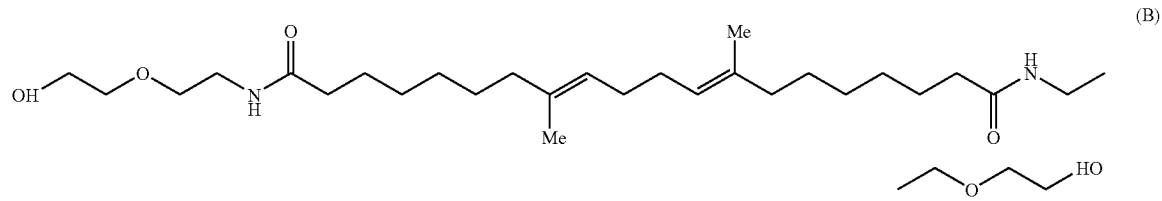

-continued

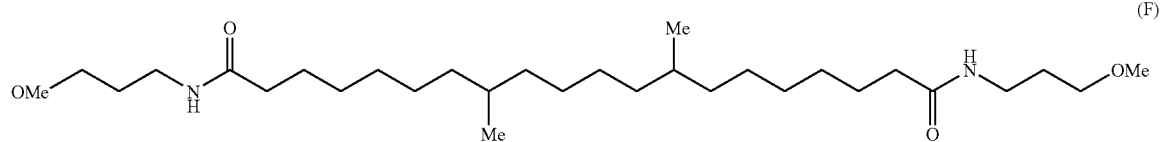

(F)

11. The hair dye composition of claim 1, wherein said diamide compound is represented by the following formula:

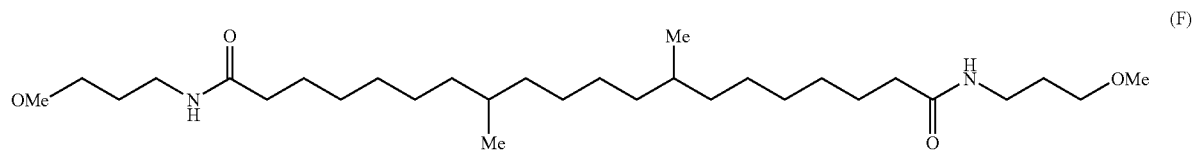

(F)

12. The hair dye composition of claim 1, wherein said dye is an oxidative dye intermediate comprising 0.01 to 5 wt. % of a developer and 0.01 to 5 wt. % of a coupler.

13. The hair dye composition of claim 1, wherein said oxidizing agent is hydrogen peroxide.

14. The hair dye composition of claim 1, wherein said oxidizing agent is at least one selected from the group consisting of hydrogen peroxide, urea peroxide, a bromate of an alkali metal and a peracid salt of an alkali metal.

15. The hair dye composition of claim 1, wherein said oxidizing agent is present in an amount of 2 to 12 wt. % in terms of hydrogen peroxide, based on the whole composition having the first part and second part mixed therein.

* * * * *

UNITED STATES PATENT AND TRADEMARK OFFICE
CERTIFICATE OF CORRECTION

PATENT NO. : 7,419,656 B2 Page 1 of 1
APPLICATION NO. : 10/417114
DATED : September 2, 2008
INVENTOR(S) : Yuji Hirano It is certified that error appears in the above-identified patent and that said Letters Patent is hereby corrected as shown below:

In claim 8, column 14, line 24: "HG Red No. 3" should read --HC Red No. 3--.

In claim 8, column 14, lines 25-27: "HG Red No. 16, HG Violet No. 2, HG Yellow No. 2, HG Yellow No 5, HG Yellow No. 6, HG Yellow No. 7, HG Yellow No. 9, HG Yellow No. 12" should read --HC Red No. 16, HC Violet No. 2, HC Yellow No. 2, HC Yellow No. 5, HC Yellow No. 6, HC Yellow No. 7, HC Yellow No. 9, HC Yellow No. 12--

Signed and Sealed this

Second Day of December, 2008

JON W. DUDAS
*Director of the United States Patent and Trademark Office*